United States Patent [19]

Barrington et al.

[11] Patent Number: 4,602,645
[45] Date of Patent: Jul. 29, 1986

[54] ATRIO-VENTRICULAR PACING CATHETER

[75] Inventors: James E. Barrington, Lexington, Mass.; John Sylvanowicz, Glens Falls, N.Y.

[73] Assignee: C. R. Bard, Inc., Murray Hill, N.J.

[21] Appl. No.: 450,215

[22] Filed: Dec. 16, 1982

[51] Int. Cl.$^4$ .............................................. A61N 1/04
[52] U.S. Cl. ................................. 128/786; 128/419 P
[58] Field of Search ............ 128/783, 784, 786, 419 P, 128/419 RG

[56] References Cited

U.S. PATENT DOCUMENTS

| | | | |
|---|---|---|---|
| 3,333,045 | 7/1967 | Fisher | 128/419 P |
| 3,416,533 | 12/1968 | Fisher et al. | 128/786 |
| 3,596,662 | 8/1971 | Bolduc | 128/786 |
| 3,865,118 | 2/1975 | Bures | 128/786 |
| 3,937,225 | 2/1976 | Schramm | 128/785 |
| 3,949,757 | 4/1976 | Sabel | 128/786 |
| 4,057,067 | 11/1977 | Lajos | 128/785 |
| 4,112,952 | 9/1978 | Thomas | 128/785 |
| 4,136,701 | 1/1979 | Barton | 128/785 |
| 4,261,847 | 6/1981 | Stokes | 252/67 |
| 4,289,138 | 9/1981 | Halvorsen | 128/642 |
| 4,289,144 | 9/1981 | Gilman | 128/785 |
| 4,332,259 | 6/1982 | McCorkle, Jr. | 128/786 |
| 4,355,646 | 10/1982 | Kallok et al. | 128/786 |
| 4,357,947 | 11/1982 | Littleford | 128/786 |
| 4,402,328 | 9/1983 | Doring | 128/419 P |
| 4,422,460 | 12/1983 | Pohndurf | 128/786 |

FOREIGN PATENT DOCUMENTS 2605590 8/1977 Fed. Rep. of Germany ... 128/419 P

*Primary Examiner*—Edward M. Coven
*Attorney, Agent, or Firm*—Wolf, Greenfield & Sacks

[57] ABSTRACT

A cardiac pacing catheter system includes a main guiding catheter and a pair of electrical leads adapted to make direct electrical contact with the ventricle and the atrium of the patient's heart. The main catheter has a pair of lumens which guide and contain the ventricular and atrial leads. Each of the leads can be advanced and manipulated separately and independently within the main catheter body. The lumen for the ventricular lead exits at a port at the distal end of the main catheter body. The lumen for the atrial lead exits along a port at the side of the catheter, at a location proximal of the distal end. The atrial lead is spring-like and is formed with a J-shaped curve at its distal end which, when it exits from the catheter lumen, will assume the J-shaped configuration so that it may be manipulated into direct contact with the more upwardly disposed roof regions of the atrium.

The device is used by advancing the catheter, containing the leads in retracted configuration, through the superior vena cava just to the entry to the right atrium. The catheter then can be secured in that position. The ventricular lead then may be extended into and through the right atrium, through the tricuspid valve and into the right ventricle to establish electrical contact at the ventricular apex. After the ventricular lead has been placed and secured the atrial lead is advanced through and out of the catheter body to extend its distal tip and enable it to assume its normally relaxed J-shaped configuration. The orientation and position of the atrial lead can be adjusted and guided with precision by manipulation from the proximal end so that the electrode tip of the atrial lead may be brought into direct electrical contact with the desired portion of the roof region of the atrium, preferably the atrial appendage.

12 Claims, 17 Drawing Figures

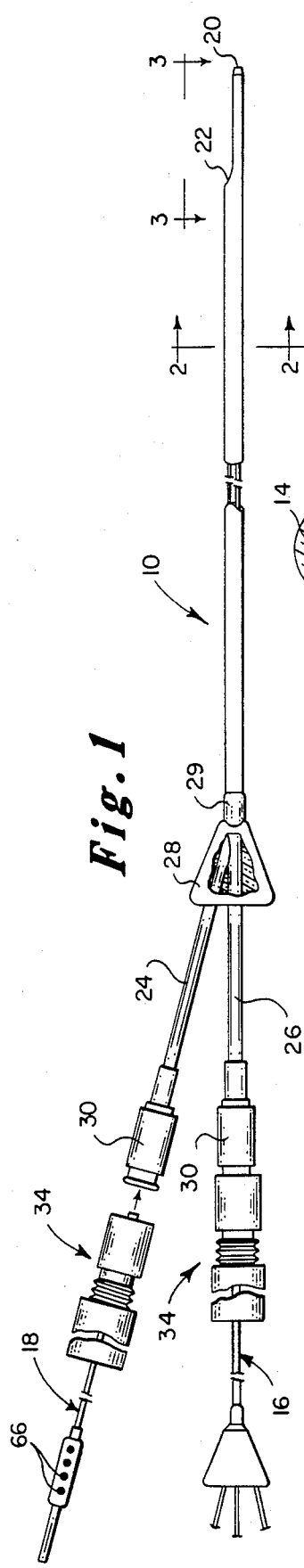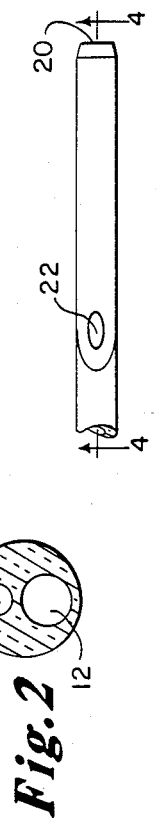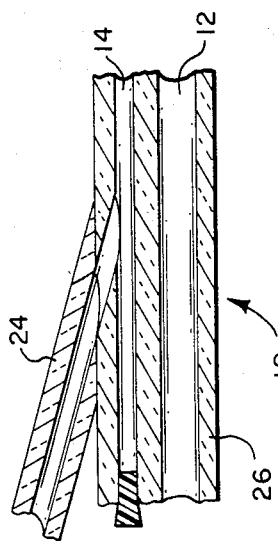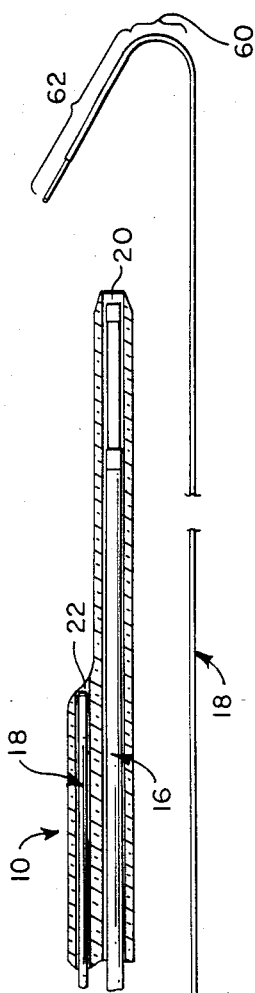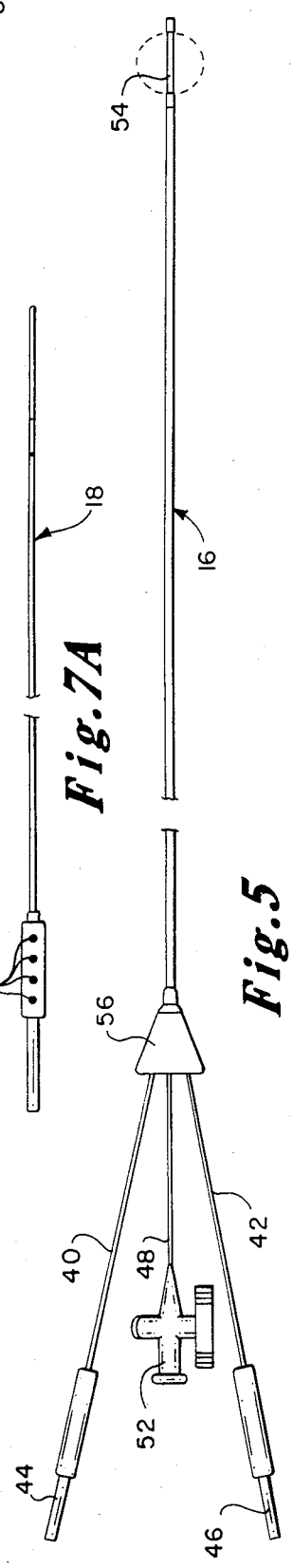

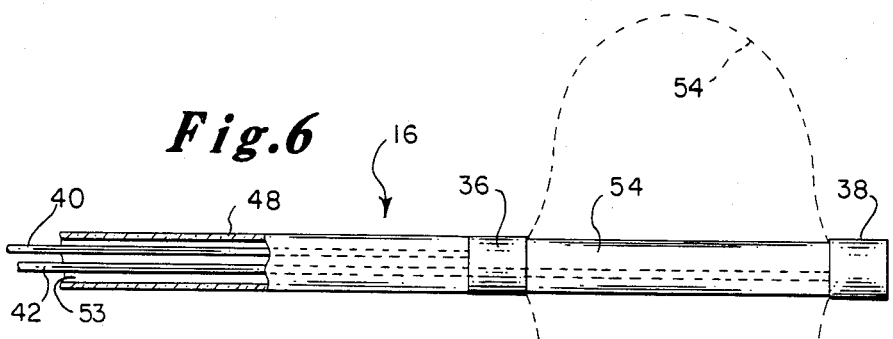
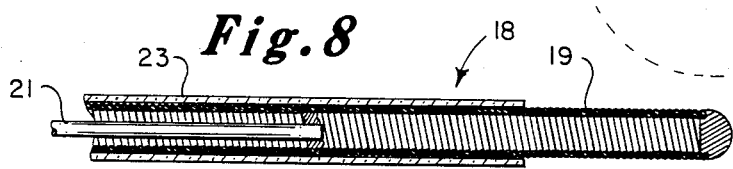
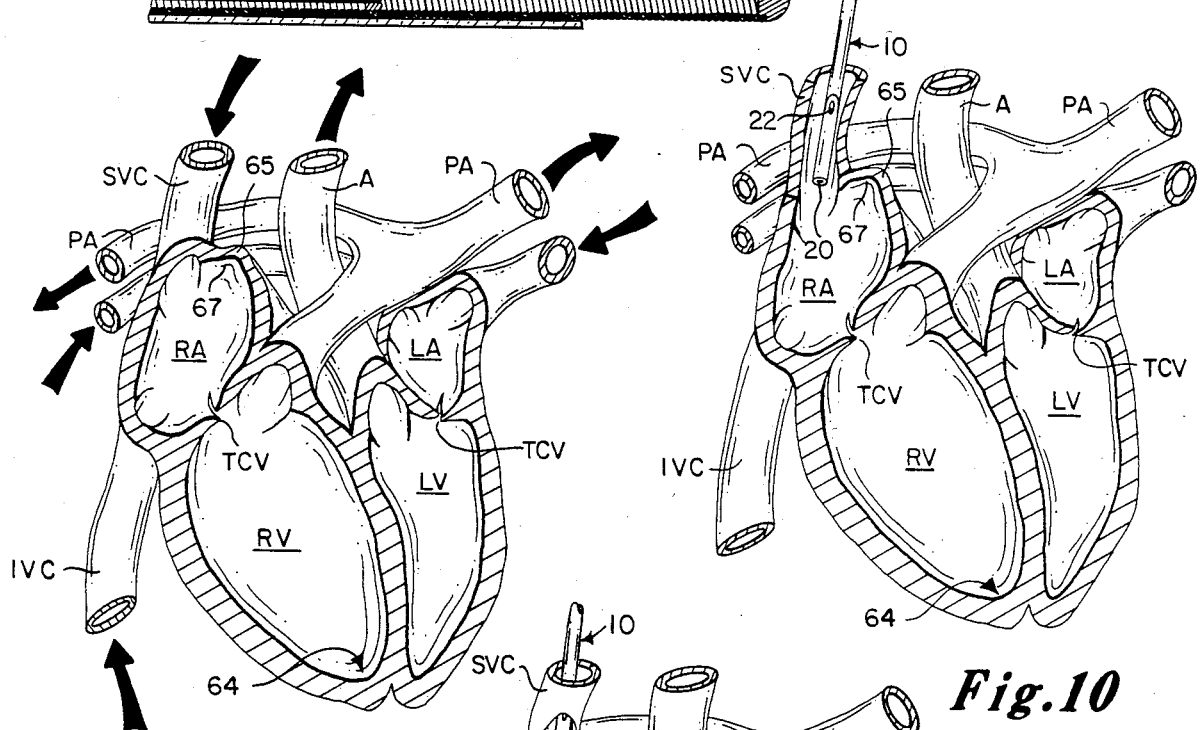

ATRIO-VENTRICULAR PACING CATHETER

BACKGROUND OF THE INVENTION

This invention relates to cardiac catheters of the type used to control a patient's heart activity by providing electrical pulses to the heart to pace the heart rhythm. The use of such catheters often may be required when heart rhythm malfunctions. By applying electrical pulses directly to the heart the rhythmic malfunction may be corrected, at least temporarily, to reestablish more regular heart activity and stabilize the patient in that condition. Such pacing techniques are used more commonly in emergency situations during post-operative care and in intensive care units for pre-operative as well as post-operative care.

Although a variety of catheters with pacing electrodes are available commercially and are in regular clinical use, they are not free from difficulty. For example, often it is important to establish electrical contact as quickly as possible, such as when trying to restore a functioning heartbeat to a patient under emergency conditions. The prior devices, however, have not lent themselves to rapid and accurate placement of the electrodes. In some techniques independent electrodes are placed separately through different veins to contact the atrium and ventricle. Other devices have bundled together a number of electrodes of different lengths arranged so that the longer electrodes will reach into the right ventricle while the shorter electrodes will reach into the right atrium.

Still other devices have been suggested, such as that in U.S. Pat. No. 3,949,757 to Sabel in which atrial and ventricular leads are contained within a sheath and in which the atrial lead is slidable with respect to the sheath so that it may be projected into surface contact with the atrium wall after the ventricular lead is placed. Although the device described in the Sabel patent appears to be more conveniently used than the prior devices, it nevertheless fails to overcome a number of remaining difficulties. For example, none of the prior devices, including Sabel, makes for any provision by which the wide variation in heart sizes of various patients may be accomodated. In this regard it is desirable, for a number of reasons, to place the electrode(s) in direct contact with the heart muscle. Moreover, it is desirable that certain regions of the ventricle and atrium (for example, the sino-atrial node) which are acutely sensitive to electrical stimulation, be contacted directly by the electrode. However, because of the wide variation, from patient to patient, of the size of the heart, no practical device has been proposed which was capable of quick and easy placement and adjustment so as to make direct contact with specific portions of the heart muscle, regardless of the size of the patient's heart.

It is desirable, when pacing a heart, to contact the most electrically sensitive areas (such as the sino-atrial node) because that enables lower energy pulses to be used. The use of lower energy pulses is desirable because it tends to create less interference and disruption with other electrically controlled functions of the heart. Until the present invention, precise and reliable placement of the leads in direct contact with selected portions of the heart could not be achieved reliably and, as a result, it often was necessary to apply relatively high energy pulses. Often the lead might not be in direct contact with the heart wall at all, much less in contact with a particularly sensitive portion of the heart wall. As a result, the higher energy pulse is necessary to overcome the impedance of the blood and the distance between the electrode and the heart wall. In addition, applying a high energy pulse also may interfere with the sensing function which often is desirable when pacing. Pacemaking equipment often includes sensing circuitry by which the electrical activity and condition of the heart may be monitored by the electrodes in the intervals between pacing pulses. The conditions sensed can be used to control the nature and timing of the pulses applied to the patient. If it is necessary to apply high energy pulses, as has been common with many of the prior devices, that tends to disrupt and interfere with the sensing function of the pacemaker.

Another important consideration in cardiac pacing is proper synchronization of atrial and ventricular functioning. Often it is desirable to pace the atrium and the ventricle in proper sequence so as to achieve as near as normal heart function as possible. This, in turn, may require placement of an electrode in each of the ventricle and the atrium and proper and precise control of the pulsing so that they operate in their normal sequence. In some types of rhythmic disorders, such as heart block, sequential pacing of both the atrium and ventricle is essential.

Still another difficulty presented with the prior art devices is the tendency for the electrode leads to become dislodged from their position in the heart as a result of the repeated flexing of the heart in its pumping action. Dislodgement or shifting of an electrode from its intended position disrupts the pulsing and/or sensing functions with potentially serious consequences.

It is among the primary objects of the invention to provide an atrio-ventricular pacing catheter which overcomes the foregoing and other difficulties.

SUMMARY OF THE INVENTION

The present invention includes a catheter assembly having a main catheter body which receives and provides a guide for a ventricular lead and an atrial lead. Each of the ventricular and atrial leads is slidable in an independent lumen formed in the catheter so that the ventricular and atrial leads are slidable independently with respect to the catheter and to each other. The lumen for the ventricular lead has an exit port at the most distal end of the main catheter. The lumen for the atrial lead has an exit port located proximally of the most distal end of the catheter.

In accordance with one of the objects of the invention, the device is arranged so that the ventricular lead may be advanced into contact with the ventricular apex and the atrial lead may be advanced into contact with the atrial appendage. The ventricular apex and atrial appendage each define somewhat concave surfaces within the heart and provide concave surfaces which tend to provide an increased degree of stability for an electrode which bears against that surface under a light spring-like pressure. The atrial appendage is located in the roof region of the atrium in close proximity to the electrically sensitive sino-atrial node. Because the sino-atrial node as well as the atrial appendage are in the roof region of the atrium, they are difficult to reach, it being among the objects of the invention to provide an improved system which facilitates making direct electrical contact with those roof regions of the atrium.

When in use, the leads are positioned in the main catheter with their distal tips located just inwardly of their respective exit ports and the assembly is advanced, in that configuration, through the patient's vein (the superior vena cava) until the distal end of the catheter is just at the entry to the right atrium. The catheter is secured in that position. The ventricular lead then is advanced through the catheter so that its distal tip may pass through the tricuspid valve of the heart and into the right ventricle. The distal end of the ventricular lead is provided with a balloon which, if the patient has any blood flow, may be inflated during the insertion procedure to help to advance the ventricular lead through the tricuspid valve and into the right ventricle with the blood flow. Once in the right ventricle the balloon is deflated so that the electrode at the distal tip of the ventricular lead can be urged into a stable position in contact with the ventricular apex. Ventricular pacing may begin immediately upon contact with the electrode(s) at the distal tip of the ventricular lead with the surface of the ventricle.

Once the ventricular lead is secured in place and is functioning to pace the patient's ventricle, the atrial lead may be placed. That is accomplished simply by manipulating the proximal end of the atrial lead to advance the atrial lead and cause the distal end to project out of the atrial lumen. In the present invention the outlet for the atrial lumen is located proximally of the outlet for the ventricular lead and the lumen is located offset from the center of the main catheter. As the atrial lead emerges from its exit port, its distal tip assumes a J-shape and it will be in a better position to reach and contact the roof region of the atrium and the concave surface of the atrial appendage. The device is arranged so that the atrial lead may be controllably manipulated from its proximal end in longitudinal as well as rotational directions. Thus, the invention provides a high degree of control in the placement of the atrial lead. The proximal end of the atrial lead is provided with suitable markings to facilitate positioning. Means (Tuehy-Borst adapters) are provided to secure the leads in their respective positions with respect to the catheter.

It is among the general objects of the invention to provide an improved atrio-ventricular pacing catheter system.

Another object of the invention is to provide an atrio-ventricular pacing catheter which can be deployed and placed rapidly.

A further object of the invention is to provide an atrio-ventricular catheter which facilitates placement of the electrical leads in stable positions in each of the ventricle and atrium.

Another object of the invention is to provide an atrio-ventricular pacing catheter which assures direct contact with the surface of the heart and which requires a low level signal for pacing.

A further object of the invention is to provide a device of the type described which may be used with equal facility with a wide range of heart sizes.

Another object of the invention is to provide a device of the type described which is easier to use than with previous devices.

Still another object of the invention is to provide a device of the type described which requires minimal adjustment but, if adjustment is required, it may be accomplished quickly and easily.

Yet another object of the invention is to provide a device for introducing two separately and independently manipulable cardiac electrodes through a single introduction site thereby reducing the chance of infection and minimizing trauma to the patient's vasculature.

DESCRIPTION OF THE DRAWINGS

The foregoing and other objects and advantages of the invention will be appreciated more fully from the following further description thereof, with reference to the accompanying drawings wherein:

FIG. 1 is an illustration, partly broken away, of the catheter assembly including the catheter containing the ventricular and atrial leads positioned as they would be when the assembly is introduced to the patient;

FIG. 1A is a sectional illustration of the bifurcation of the catheter;

FIG. 2 is a cross-section of the catheter assembly as seen along line 2—2 of FIG. 1;

FIG. 3 is a plan illustration of the distal portion of the catheter as seen along the line 3—3 of FIG. 1;

FIG. 4 is an enlarged sectional illustration of the distal portion of the catheter as seen along the line 4—4 of FIG. 3 and illustrating the positions of the distal ends of the ventricular and atrial leads when the assembly is introduced into the patient;

FIG. 5 is an illustration of the ventricular lead showing, in phantom, a flow assist balloon in its inflated configuration;

FIG. 6 is an enlarged illustration of the distal end of the ventricular lead;

FIG. 7 is an illustration of the atrial lead;

FIG. 7A is an illustration of the proximal and distal ends of the atrial lead showing the plane of the relaxed curved distal end and its alignment with indicia at the proximal end;

FIG. 8 is an enlarged illustration of the distal tip of the atrial lead;

FIGS. 9-16 illustrate diagramatically portions of a patient's heart and the manner in which the present invention is used.

DESCRIPTION OF THE PREFERRED EMBODIMENT

Figure 12:
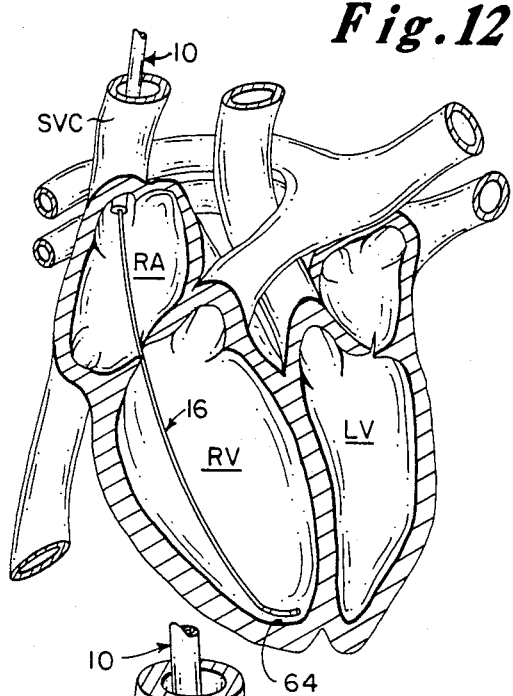

As shown in FIG. 1 the catheter assembly includes a main catheter 10 which may be extruded from an appropriate plastic material such as a fluoroethylene polymer. The main catheter 10 is formed with a pair of lumens, including a ventricular lead lumen 12 and an atrial lead lumen 14. The ventricular lead lumen 12 is larger in diameter than the atrial lead lumen 14 and is intended to receive the relatively larger diameter ventricular lead 16. The smaller lumen 14 slidably receives the atrial lead, indicated generally at 18. The lumens 12, 14 are arranged side-by-side with at least the atrial lumen 14 being displaced from the central axis of the main catheter 10.

The ventricular lumen 12 extends fully along the length of the main catheter 10 and terminates in an exit port 20 at the distal tip of the main catheter 10. The atrial lead lumen 14 terminates in an exit port 22 which is spaced proximally from the distal end of the catheter 10. In the preferred embodiment of the invention the exit port 22 for the atrial lead 18 is disposed approximately one centimeter proximally of the ventricular lead outlet 20. When the atrial lead 18 is advanced through the lumen 14, it will emerge from exit port 22 before reaching the distal tip of the catheter 10 and, as will be described, will assume a J-shaped configuration as it emerges from the exit port 22.

The proximal portion of the main catheter 10 is bifurcated to include and define an atrial guide tube 24 and a ventricular guide tube 26. The ventricular guide tube 26 may be defined by a continuation of the main catheter 10 with the atrial lead lumen 14 obstructed. The atrial guide tube 24 may be formed from a separate tube which is spliced to the main catheter 10 so that it communicates only with the atrial lead lumen 14 as suggested in FIG. 1A. The spliced region may be encapsulated in a molded plastic fitting 28. The distal portion 29 of the molded fitting 28 preferably is formed with a taper so that it may be detachably locked to corresponding fitting on a catheter introducer.

The proximal end of each of the atrial and ventricular guide tubes 24, 26 preferably is provided with a standard luer fitting 30. Each of the luer fittings 30 preferably is provided with a lockable, sealing fitting indicated at 34, such as, for example, a Tuehy-Borst fitting. The fittings 34 enable an element, such as the atrial or ventricular lead to be passed through the fitting and then tightened to lock the leads 16, 18 in place and effect a seal about the lead.

The ventricular lead 16 is shown in further detail in FIGS. 5 and 6. It is substantially longer than the guide catheter 10 and, for example, may be of the order of fifty centimeters long. The lead 16 may be formed from a slender tube 48 of extruded plastic with insulated electrical wires 40, 42 carried in the tube 48. As shown in further detail in FIG. 6 the ventricular lead 16, in accordance with the present invention, is bipolar, having a pair of spaced ring electrodes 36, 38 at its distal end. Each of the electrodes 36, 38 is electrically connected to insulated wires 40, 42 which emerge at the proximal end of the lead and terminate in connectors 44, 46 (see FIG. 5). The tube 48 emerges at the proximal end of the ventricular lead and is connected to a stopcock 52. The tube 48 thus also defines an inflation lumen 53 for a balloon 54 which is attached to the distal end of the lead, between the ring electrodes 36, 38. The ventricular lead is provided with a molded plastic member 56 at the trifurcated region of the tube 48 and wires 40, 42. As will be described in further detail, the balloon 54 may be inflated to facilitate guidance of the ventricular lead into proper placement and advancement through the tricuspid valve and into engagement with the ventricular apex.

The atrial lead 18 is illustrated in FIGS. 7 and 8 and may be about forty centimeters long. The lead 18 is illustrated as being monopolar and formed from a wound spring wire 19 having a central core wire 21 similar to conventional construction for a spring guide. The core wire, however, terminates approximately eight millimeters from the distal tip of the lead so that the distal region will be soft and flexible. The proximal end of the atrial lead includes a connector plug 58 for attachment to a pacemaker. The atrial lead 18 is covered, along its length, with an insulative jacket 23 which may be formed from a shrinkable plastic, shrunk onto the spring wound lead. The jacket 23 may be formed, for example, from TFE plastic and covers all of the lead except for the most distal five millimeters which serves as the atrial electrode.

As shown in FIG. 7 the distal end of the atrial lead 18 is formed so that when in a relaxed state it will assume somewhat of a J-shaped configuration having a curved segment 60 and a most distal straight segment 62. The curved segment 60 extends through an arc of approximately 150°. The diameter of the atrial lead 18 is approximately 2 French (0.026") and, therefore, is flexible so that the atrial lead 18 can flex easily to a straight configuration so as to be contained fully and be slidable easily within the atrial lead lumen 14 of the main catheter 10.

Figure 13:
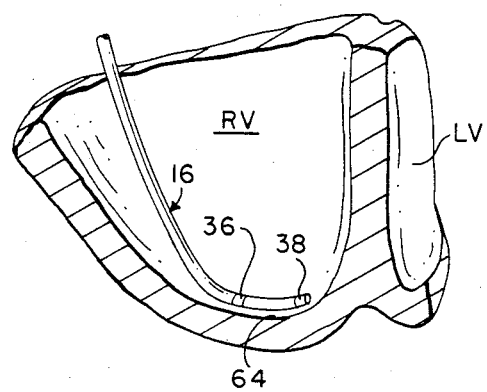
Figure 15:
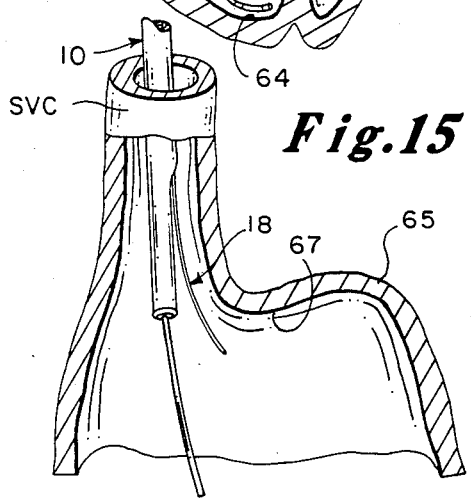
Figure 16:
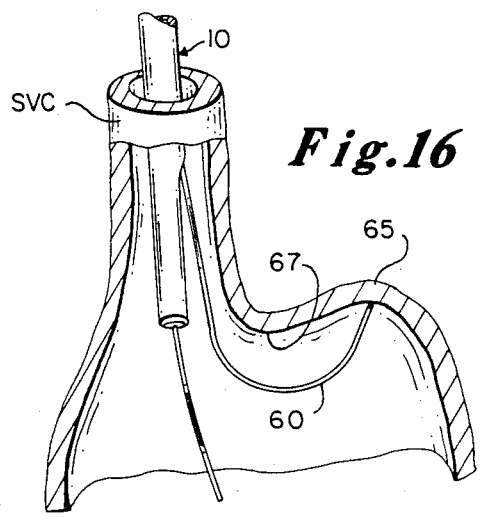
Figure 14:
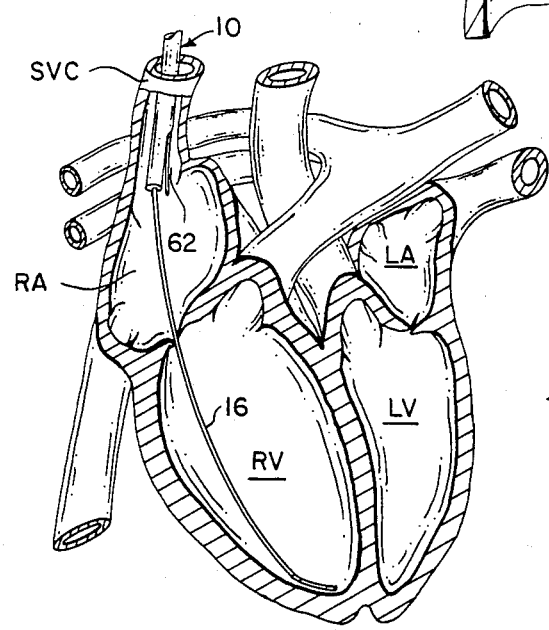

The manner in which the invention may be used is described with reference to FIGS. 9–16 which illustrate the human heart and the various positions of the distal portions of the main catheter 10 and leads 16, 18. As suggested diagrammatically in FIG. 9, in a properly functioning heart blood returns from the venous system through the superior vena cava (identified as SVC in the drawings) and inferior vena cava (IVC) the right atrium (RA) of the heart. When the right atrium contracts it pumps blood through the one-way tricuspid valve (TCV) and into the right ventricle (RV). The right ventricle (RV) then contracts to close the tricuspid valve (TCV) under pressure and to pump blood through the pulmonary arteries (PA) to the lungs where the blood is oxygenated. The oxygenated blood then flows through the pulmonary veins to the left atrium (LA), through the mitral valve MV and then into the left ventricle (LV). The left ventricle pumps blood through the aorta (A) throughout the body and then through the venous system to return the blood to the heart and renew the cycle.

One facet of the invention relates to the ability of the leads to be placed in concave portions of the atrium and ventricle which will tend to retain the electrodes in a stable position so that the electrodes will not become dislodged as the heart flexes and pumps repeatedly. To that end, the present invention contemplates engaging the ventricular lead with the ventricular apex at the lowermost portion of the right ventricle as indicated at 64 in FIG. 9. The ventricular apex is concave and provides a stable location from which the electrodes at the end of the ventricular lead will not become dislodged from their contact with the heart wall. The ventricular apex 64 is considered a satisfactory location in which to make electrical contact between the ventricular lead both for pacing and sensing functions.

In accordance with the present invention the portion of the right atrium which most desirably is contacted with the atrial lead is the atrial appendage 65, a portion of the heart which is located in the roof region of the atrium which defines a concave surface, as would be seen from within the atrium. Although the atrial appendage 65 is not as sensitive electrically as the sino-atrio node, (indicated at 67 in FIG. 9) it is adjacent to the sino-atrio node and, therefore, is close enough to it so as to provide substantially low impedance for the pacing and sensing signals to be highly effective. The atrial appendage 65 is a relatively delicate membranous portion of the heart and it is important, therefore, that the atrial lead be constructed to that it will make contact in a very delicate manner.

Normally the self-regulating electrical activity of the heart causes the right atrium RA and right ventricle RV to contract in sequence, with the right atrium RA contracting first to pump blood through the tricuspid valve TVC and into the right ventricle RV, with the right ventricle RV contracting after a short delay. The delay in the contractions of the right atrium RA and right ventricle RV are sufficient to enable the atrium to pump blood through the tricuspid valve TCV and into the right ventricle RV.

Various disorders can occur with respect to the electrical control of the heart's function. Typically, when there is a disruption in the normal electrical activity of the heart, it is essential first to reestablish a regular rhythm in the right ventricle so as to maintain at least a sufficient flow of blood to the lungs so as to provide at least a minimally sufficient supply of oxygenated blood to the patient. It is preferred, and in some instances it is necessary, also to establish a proper sequential rhythm for the atrium so as to maximize the pumping efficiency of the heart. Thus, as soon as possible after the ventricular lead has been placed and pacing has begun, it is desirable to place and begin pacing with the atrial lead.

The catheter 10 of the present invention is introduced intravenously, preferably through the internal jugular or subclavian vein which leads to the superior vena cava SVC. Any of a variety of well-known techniques may be employed, such as inserting a catheter introducer percutaneously to provide access to the vein. The device is arranged so that the leads 16, 18 are within their respective lumens 12, 14, with their distal ends located just proximally of their openings 20, 22, (as suggested in FIG. 4) in readiness to be advanced. The assembly, with leads so positioned, is advanced through the catheter introducer until the distal tip of the catheter is at the region of the juncture between the superior vena cava SVC and the right atrium RA as illustrated in FIG. 10. The procedure preferably is monitored on a fluoroscope from which the positioning of the various elements can be verified. The assembly should be positioned so that the outlet port 22 of the catheter 10, from which the distal end of the atrial lead will emerge, is sufficiently close to or just within the atrium so as to assure that the atrial lead will advance and extend properly into the upper region of the atrium, as will be described. When the catheter 10 is positioned properly, it is secured in place by any of a number of means, such as by taping it firmly to the patient or by securing the tapered portion 29 of fitting 28 to the conventional fitting at the proximal end of the introducer, or by a combination. Once the guide catheter 10 is placed, it will not have to be moved again, until it is to be removed.

The ventricular lead 16 then is advanced, the sealing gland 34 first being released to free the ventricular lead for movement. If the balloon is to be inflated, as suggested in FIG. 11, the ventricular lead 16 then is advanced slightly to project the balloon tip outwardly beyond the distal opening 20. The balloon may be inflated with carbon dioxide gas by a syringe connected to the stopcock 52. With the balloon inflated, the ventricular lead is advanced through the main catheter 10. The balloon, when used, flows with the blood flow and provides assured guidance that the ventricular lead 16 will flow to and through the tricuspid valve TCV into the right ventricle RV instead of passing downwardly into the inferior vena cava IVC or at some other angle. The balloon may be used with some effectiveness only when the heart has some pumping function and there is some blood flow. When there is no pumping function and no blood flow the system may be used without inflating the balloon.

Once the distal end of the ventricular lead is in the right ventricle RV (as suggested in phantom in FIG. 11) the balloon is deflated (if it was previously inflated) and the distal end of the ventricular lead is advanced into the pocket-like ventricular apex 64. The ventricular lead is advanced to the position shown in FIG. 12 in which it is assured that its distal end has been bent so that both ring electrodes 36, 38 are in contact with the heart muscle, in the region of the apex 64 as shown in enlarged detail in FIG. 13. Proper electrical contact with the ring electrodes 36, 38 can be assured by monitoring the electrical pacing device and sensing feedback signals indicative of the proper electrical contact. When the surgeon is satisfied that the ventricular lead 16 is properly placed, securely contained within the pocket defined by the ventricular apex and in good direct electrical contact with the heart, the ventricular lead is locked in place by fastening the Tuehy-Borst adapter 34.

In the illustrative embodiment, the preferred electrode configuration for the ventricular lead is bipolar, that is, there are two ring electrodes 36, 38 which will contact electrically the surface of the heart muscle, at the ventricular apex. By apply a pulse across these two closely spaced electrodes, only that portion of the heart which is in the region of the electrodes is affected by the pulse. Because electrical activity within the heart muscle is very complex it is desirable to apply pulses only at a location and of an energy level which will be sufficient to pace the heart but without disrupting any other electrical function of the heart. Thus, with the bipolar ventricular lead shown in the illustrative embodiment, electrical energy is applied only to the heart in a small localized region sufficient to pace and to sense the activity of the right ventricle and without affecting other portions of the heart's electrical activity.

After the ventricular lead 16 has been placed, the atrial lead 18 is placed. The sealing gland 34 associated with the atrial lead is unlocked and the atrial lead 18 is advanced so that its distal end emerges from the outlet port 22. As the atrial lead emerges, the most distal straight segment 62 will emerge, paralleling the catheter 10, as suggested in FIG. 14. As advancement of the atrial lead continues, the curved segment 60 begins to emerge from the outlet port 22 and the lead begins to assume its J-shape as suggested in FIG. 15. Before the atrial lead expands to its normally relaxed, full J-configuration, the distal tiip will engage and drag against the uppermost roof surfaces of the right atrium RA, as suggested in FIG. 16. Further advancement of the atrial lead will project it most distally out of the exit port 22 and downwardly fron the roof of the atrium until it assumes a fully relaxed configuration. The surgeon then may control the position of the atrial lead by manipulating it from its proximal end, both longitudinally and rotationally. By such manipulation the surgeon can place the electrode at the distal tip at precisely the location on the roof region of the atrium as he desires. This enables the surgeon to place the atrial electrode precisely against the concave atrial appendage. As described above, the atrial appendage defines somewhat of a concave socket which provides a stable location for electrode contact. The surgeon can verify that contact has been made with the atrial appendage by monitoring feedback of electrical signals. When the surgeon is satisfied that the atrial lead is in proper contact, the Tuehy Borst adapter is tightened down about the atrial lead to secure it in position.

The foregoing description of the atrial lead has related to a monopolar configuration, in which the distalmost tip defines a single electrode. A grounding electrode for use with the monopolar electrode may be in the form of an externally applied electrode patch such as the type commonly used in electrocardiogram procedures. Alternately, the atrial lead may be formed so as to be bipolar, in similar manner to the bipolar configuration of the ventricular lead. Whether monopolar or bipolar, it is important that the distal tip of the atrial lead be flexible and resilient to assure avoidance of trauma to the delicate membranes in the roof region of the atrium.

With the main catheter 10 and both leads 16, 18 secured in position, and particularly when the ventricular and atrial leads are in engagement with the ventricular apex and atrial appendage, respectively, the concave contacting regions materially reduce the chances of the leads becoming dislodged under the influence of the pumping action of the heart.

From the foregoing it will be appreciated that the present invention may be used with all patients, regardless of variations in heart size, because each of the leads is positioned independently with respect to each other and also independently with respect to the catheter.

Means also are provided to facilitate positioning and orientation of the atrial lead by reference to the relative position of the proximal end of the lead as compared to the catheter 10. To that end, the proximal end of the atrial lead preferably is marked with indicia indicated at 66 in FIG. 7A to indicate the radial plane in which the distal end portions 60, 62 of the atrial lead project. By comparing the portion of marking 66 with the position of the guide tube 24, or some other indicia indicating the side of the guide catherer 10 where the outlet port 22 is located, the surgeon can determine the relative angular position of the distal end of the atrial lead with respect to the main catheter and, therefore, with respect to the patient's heart. By using such reference points the surgeon will be able to direct the distal end of the atrial lead into close proximity, if not precise contact with the atrial appendage quickly and with minimal manipulation.

Also among the features of the invention is the relative location of the exit port 22 with respect to the distal tip of the catheter 10. When the catheter 10 is positioned so that its distal tip 20 is located just at the juncture of the superior vena cava SVC and the right atrium RA, the exit port 22 for the atrial lead will be located somewhat within the superior vena cava. However, as the atrial lead emerges from the opening 22 it advances substantially along and parallel to the catheter 10 and begins to assume its curl just as the electrode tip of the atrial lead enters into the upper portion of the atrium. Thus, as the atrial lead is advanced it will begin its curl in close proximity to the roof of the atrium and will contact and brush against the roof of the atrium before it assumes its fully opened J-configuration. If the surgeon has advanced the atrial lead in a rotative position which would cause the atrial electrode to contact the atrial appendage directly, then the atrial lead may be secured in that position immediately. Otherwise, the atrial lead may be advanced further into the atrium, to enable the J to expand fully, free of the atrial wall, so that the surgeon can rotate the atrial lead to the desired angular position and then draw the lead proximally to bring it into contact with the atrial appendage.

From the foregoing it will be appreciated that the present invention provides significant advantages over the prior art and the presently employed systems. The system can be used with equal effectiveness on any patient regardless of the size of the patient's heart. It enables rapid deployment of the ventricular and atrial leads in sequence. It enables both ventricular lead and atrial lead to contact concave regions of the ventricle and atrium respectively, and particularly the atrial appendage of the right atrium to assure the mechanically stable positioning of both ventricular and atrial leads so that they will not likely be dislodged as a result of pumping action of the heart. Moreover, these advantages are achieved in a pacing/sensor catheter in which the electrodes make direct contact with the endocardium thereby reducing the amount of power which must be applied to the leads and enabling more precise control of the pacing and sensing functions.

It should be understood, however, that the foregoing description of the invention is intended merely to be illustrative and that other embodiments and modifications may be apparent to those skilled in the art without departing from its spirit.

Having thus described the invention what I desired to claim and secure by Letters Patent is:

1. A rapidly placeable, percutaneously insertable catheter assembly for temporary emergency atrio-ventricular pacing comprising, in combination:

a cathether having proximal and distal ends and having a first lumen with an outlet port at the distal end of the catheter and a second lumen having an outlet port at the distal region of the catheter, the outlet port of the second lumen being disposed proximally of the outlet port of the first lumen;

a ventricular lead having a proximal end and a distal end and being slidably received within the first lumen of the catheter, said ventricular lead being longer than said first lumen said ventricular lead having electrode means at its distal end;

an atrial lead slidably received within the second lumen, the atrial lead being longer than said second lumen and having a distal end which is shaped so that it will assume a predetermined curve when in a relaxed configuration; the dimensions and flexibility of the atrial lead being such as to enable the distal end of the atrial lead to straighten when withdrawn into the second lumen and to return to its curved shape when projected out of the second lumen;

each of said leads being individually positionable longitudinally with respect to the catheter and each other;

said curved configuration for the distal end of the atrial lead having a first, arcuate, segment circumscribing an arc of approximately 150° and a second, straight segment extending from the distal end of the arcuate segment, the second segment being approximately 15 millimeters in length, the distal portion of the second segment including an exposed electrode;

quick-releasable sealing and locking means associated with the proximal end of the catheter for gripping and locking said leads in selected positions and in sealed relation to the catheter and for releasing said gripping and sealing to permit repositioning of the leads;

said catheter assembly being constructed and arranged to enable the catheter with said ventricular and atrial leads in place in said lumens to be inserted percutaneously and rapidly as a unit into a patient's venous system.

2. A catheter assembly as defined in claim 1 wherein said second lumen is offset from the central axis of the catheter.

3. An assembly as defined in claim 1 further comprising:

the proximal end of the catheter being formed to define a bifurcation, said bifurcation including tubular guide means for communication with each of the first and second lumens;

said quick releasable sealing and locking means being associated with each of the tubular guide means.

4. A catheter assembly as defined in claim 1 wherein the most distal portion of the second segment is more flexible and resilient than the more proximal portions thereof.

5. A catheter assembly as defined in claim 1 wherein said ventricular lead further comprises:

a bipolar electrode having a pair of spaced electrodes at the distal end.

6. A catheter assembly as defined in claim 5 further comprising:

an inflatable balloon at the distal end of the ventricular lead for flow assist purposes to guide the ventricular lead along the flow path through the tricuspid valve of the heart; and means in communication with the proximal end of the ventricular lead for inflating and deflating the balloon.

7. A catheter assembly as defined in claim 1 wherein the outlet port for the second lumen is approximately one centimeter proximal of the outlet port for the first lumen.

8. A catheter assembly as defined in claim 1 wherein the distal end of the atrial lead further comprises said straight segment being of a length no shorter than the distance between the outlet ports of said first and second lumens.

9. A catheter assembly as defined in claim 1 further comprising:

the atrial lead having proximal and distal ends and being constructed so that its predetermined curve at its distal and lies substantially in a plane, and indicia means at the proximal end of the atrial lead corresponding to and providing an indication of the rotational orientation of the curve.

10. A catheter assembly as defined in claim 1 wherein the atrial lead has a diameter of approximately 2 French.

11. A technique for rapid and emergency percutaneous placement of leads for atrio-ventricular pacing and sensing comprising:

providing an assembly of a guide catheter, a ventricular lead and an atrial lead, said guide catheter having a first lumen having a distal exit port and a second lumen having a distal exit port which is disposed proximally of the exit port of the first lumen, said assembly further comprising said ventricular lead being located within the first lumen and said atrial lead being located within the second lumen;

percutaneously inserting the assembly into a patient's venous system and advancing said assembly therethrough with the exit port of the first lumen disposed substantially at the entry to the right atrium;

securing the catheter in place;

advancing the ventricular lead through the first lumen, through the right atrium and tricuspid valve into the right ventricle and into engagement with right ventricular apex;

securing the ventricular lead in place and applying electrical pacing signals to the ventricular lead;

said atrial lead having a curl at its distal end and an electrode at its distal tip;

advancing the atrial lead through the second lumen to cause the curl to project out of the exit port of the second lumen whereby the curled end of the atrial lead may assume a curled configuration in which the most distal tip of the atrial lead will be disposed distally of the distal end of the guide catheter and will be engagable with the upper roof region of the right atrium;

manipulating the atrial lead longitudinally and rotationally to locate it and cause engagement of its distal electrode tip with a selected portion of the upper roof region of the right atrium; and securing the atrial lead in place.

12. A technique as defined in claim 11 further comprising applying selected electrical signals to each of the leads.

* * * * *